United States Patent [19]

McNaughton et al.

[11] Patent Number: 5,305,747
[45] Date of Patent: Apr. 26, 1994

[54] OPTICAL ELEMENTS FOR APPLANATION TONOMETERS

[75] Inventors: John McNaughton, Harlow; Jack Balzano, West Drayton, both of England

[73] Assignee: Clement Clarke International Ltd., Essex, England

[21] Appl. No.: 835,869

[22] Filed: Feb. 18, 1992

[30] Foreign Application Priority Data

Feb. 18, 1991 [GB] United Kingdom ............... 9103360

[51] Int. Cl.$^5$ ............................................. A61B 6/00
[52] U.S. Cl. ............................. 128/652; 359/837
[58] Field of Search ................. 128/645, 652, 9; 359/837

[56] References Cited

U.S. PATENT DOCUMENTS

| | | | |
|---|---|---|---|
| 3,070,997 | 1/1963 | Papritz et al. | 128/652 |
| 3,470,736 | 10/1969 | Bartfay | 128/652 |
| 3,840,004 | 10/1974 | Heine | 128/9 |
| 4,766,886 | 8/1988 | Juhn | 128/9 |

*Primary Examiner*—Randy C. Shay
*Attorney, Agent, or Firm*—Burns, Doane, Swecker & Mathis

[57] ABSTRACT

An applanating member is provided for use in an applanation tonometer and comprises an optical element replaceably held in a tubular carrier. The element is formed as a replaceable plastics moulding with integral means for locating it in the member axially and rotationally. Such an optical element can be used disposably so as to achieve higher standards of hygiene without excessive costs.

12 Claims, 1 Drawing Sheet

OPTICAL ELEMENTS FOR APPLANATION TONOMETERS

BACKGROUND OF THE INVENTION

This invention relates to instruments for the measurement of intraocular pressures, known as tonometers, and in particular to applanation tonometers.

In an applanation tonometer the eye is observed through an applanating member which is applied against the eye with sufficient pressure to flatten a predetermined are of the surface of the cornea, so that the applied pressure is able to provide a measure of the intraocular pressure.

A known applanation tonometer is described in GB 862920, the contents of which are incorporated herein by reference. The applanating member comprises a doubling prism which produces a split image of a circular area of the eye against which the member is applied, the two semi-circular part images being relatively displaced as the pressure of application changes. A convenient datum position indicating that a specific area has been flattened is obtained when the two semi-circles are seen as a continuous S-line, as is explained in GB 862920.

The doubling prism is part of a sealed unit that forms the applanating member, the prism being sealed into the forward end of a tubular carrier, the rear end of which is sealed by a plane transparent plate. Because the applanating member is the only part of the tonometer that comes into direct contact with the patient, producing the member as a sealed unit that is detachable from the instrument make periodic sterilisation more convenient. More recently, however, stricter hygiene standards have created problems in this respect. In particular, it is significant that both the *herpes simplex* virus and the HIV virus have been found in tear fluids. Since the patient's tear fluid may be left on the applanating member there could be a risk of cross-infection if the member is not fully sterilised after use on each patient. To stock sufficient applanating members to allow for the time they are out of use creates a significant burden of cost, in addition to the cost of the sterilisation process itself. It would therefore be desirable to be able to limit the costs of meeting these stricter standards.

SUMMARY OF THE INVENTION

According to one aspect of the present invention there is provided an applanating member for an applanation tonometer, comprising a tubular carrier having an optical element releasably held in and projecting forwardly from a forward end of the tubular carrier, said element being formed as a moulding comprising a substantially flat front face and a split field arrangement of prisms towards its rear end.

According to another aspect of the invention, an applanating member is provided comprising an optical element replaceably held by a tubular carrier, said element comprising a cylindrical body slidably received in an open forward end of the tubular carrier, abutment means for limiting the insertion of the element in said open end with said cylindrical body partially projecting outwardly therefrom, said body having a generally planar front face on its projecting end and having on its opposite end within the carrier a pair of optical prisms located on either side of a plane perpendicular to said planar front face.

In such a member the optical element can be a disposable part. If it is a directly moulded component, e.g. from an acrylic plastics material, it can be provided very economically and it can be replaced after each patient without little expense. While a moulding may not provide the same optical quality as a machined optical element of a conventional applanating member, it is found that it can produce results that are sufficiently good in all but a few per cent of cases. It may be desirable, however, to polish the front face of the optical element, primarily for safety reasons as it makes contact with the eye.

The invention also provides a replaceable optical element for an applanating member according to the invention. In the element, the abutment means may be provided by a flange intermediate the length of the cylindrical body that locates against the open end of the carrier. The flange may be given a considerable radial depth, e.g. having an outer diameter at least 50% greater than the diameter of the cylindrical body, and preferably substantially twice the body diameter. The element can then be easily held by the flange when it is being inserted into the carrier, so avoiding risk of contaminating the front face that forms the applanating surface. Preferably, the flange is inclined away from the front face, so as to provide a deflecting forward face for the eyelashes if the patient blinks while the element is applied against the eye.

One embodiment of the invention will be described in more detail by way of example, with reference to the accompanying drawings.

DESCRIPTION OF THE PREFERRED EMBODIMENT

Figure 1:
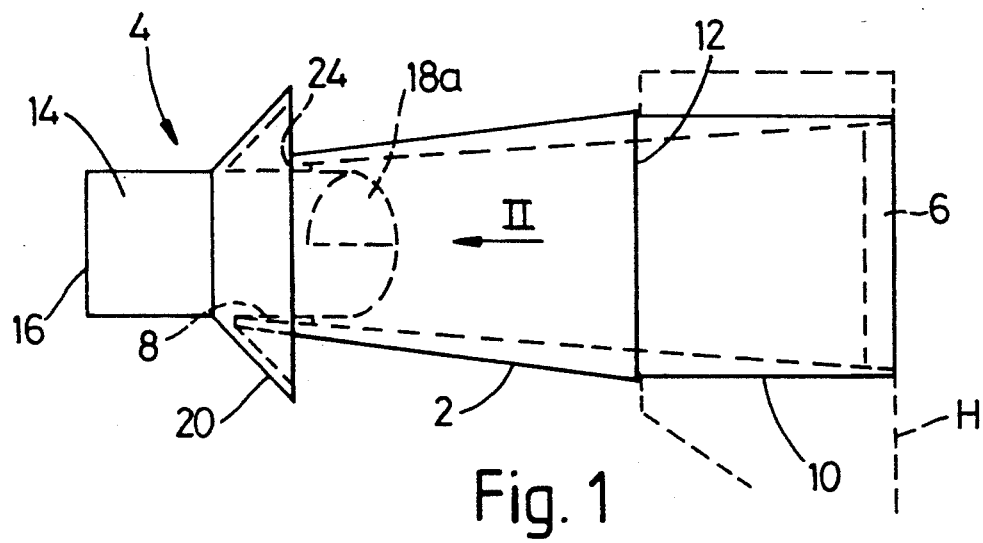
FIG. 1 is a side view of an applanating member according to the invention.
Figure 2:
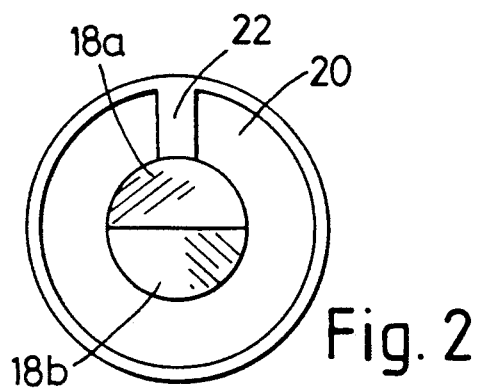
FIG. 2 is an end view in the direction of the arrow II of the optical element of the member in FIG. 1.
Figure 3:
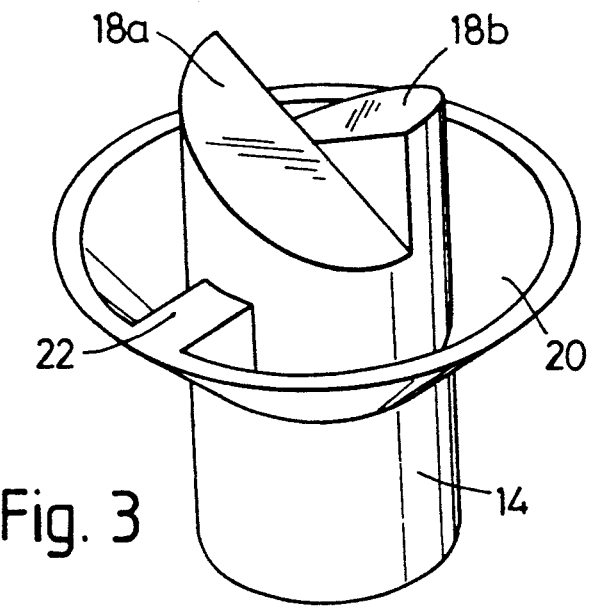
FIG. 3 is an oblique view of the optical element.

FIG. 1 shows the applanating member with an opaque tubular body 2 of circular cross-section, an optical element 4 mounted in the front opening of the body and a transparent plate 6 sealing the rear opening of the body. Adjacent its front opening the body has a cylindrical inner wall 8 in which the optical element 4 is a sliding fit. The rear cylindrical portion 10 of the body is received in a holder H of the tonometer and a shoulder 12 provides a locating abutment for the member against that holder. The holder H and the main body of the instrument may be of known design and construction and need not be further described here for an understanding of the present invention. Further details may be learned from GB 862920.

The optical element 4 is an injection moulding in a transparent material, e.g. an acrylic resin. It comprises a circular cylindrical body 14 having a flat front face 16 that provides an applanating surface and a rear face that is formed with a pair of flat, oppositely inclined faces 18a,18b adjoining each other at a central diametrical plane perpendicular to the front face and to which they themselves are perpendicular. The formation of the rear face gives the element a pair of semi-circular prisms that have the effect of producing a split field from the illumination passing through the element from the front face.

Between the front and rear faces 16,18a,18b the optical element has a peripheral conical flange 20 that is inclined rearwardly away from the front face 16. When the optical element 4 is in place in the body 2 the root of the flange 20 rests against the front edge of the body and ensures that the optical axis of the element is coincidental with the central axis of the body. In this way, the fit between the element 4 and the cylindrical inner wall 8 can be left sufficiently free to not impede the replacement of the element. Between the cylindrical body 14 of the element and the flange 20 there is a radial rib 22 which fits a complementary slot 24 in the front opening of the tubular body 2 to locate the optical element, and thereby the prism faces 18a, 18b, angularly relative to the body 2.

The flange 20 of the optical element provides a convenient gripping surface when the element is inserted in the holder, well spaced from the applanating surface so that contamination of that surface is avoided. The conical front face of the flange helps to ensure that the eyelid and eyelashes are not harmed in any way if the patient blinks while the applanating surface is applied to the eye.

The applanating member may be arranged so that it can be substituted in an existing tonometer in place of its conventional counterpart that has a permanent optical element and it can be employed in an essentially identical way. Known applanating members are often provided with external indicating means to show the orientation of the dividing plane of the split field, and such indicating means can be provided on the body 2, since the element 4 is oriented in the body by the rib 22, if it is required.

Only the front face 16 of the plastics moulding for the optical element is subjected to any subsequent machining, it being polished to ensure its smoothness in order not to risk damaging the corneal surface of the eye. Although the polishing of the front face only, does not give an image of the same quality as the conventional applanating member, it is found surprisingly that the imaging quality of the optical element is acceptable for most of the uses of an applanation tonometer. An extremely cost-effective disposable optical element can thus be provided.

We claim:

1. An applanating member for an applanation tonometer, said applanating member comprising a tubular carrier and an optical element mounted in said carrier to be applied against the eye of a subject, said optical element being releasably held in and projecting forwardly from the tubular carrier, said element being a molding having a generally cylindrical body and a radial projection intermediate the length of said body spaced from a front face of said element, the projection being in the form of a peripheral flange extending radially outwardly at an angle to the cylindrical body and inclined rearwardly away from said front face, said flange providing an abutting engagement for the optical element with the tubular carrier for locating the element longitudinally in the carrier wherein the optical element and the carrier comprise mutually co-operating location elements for locating the member angularly in the carrier, said location element of the optical element being spaced from said front face.

2. An applanating member according to claim 1 wherein the body and the flange have respective radial dimensions of which a radial dimension of the flange is at least 50% greater than the radial dimensions of the body.

3. An applanating member as claimed in claim 1, wherein said front face is substantially flat and a rear region of said optical element which is remote from said front face includes a pair of optical prisms located on either side of plane which is perpendicular to the front face.

4. An applanating member for an applanation tonometer according to claim 1, wherein said flange includes a front face and a rear face extending away from said cylindrical body, said rear face forming with said body an annular pocket for receiving the tubular carrier.

5. An applanating member for an applanation tonometer, said member comprising an optical element and means for supporting said element releasably in a lever arm of the tonometer, said optical element comprising a cylindrical body having a generally planar face at a front end of said body, a split field arrangement at a rear region of said body remote from said front end, said split field arrangement comprising a pair of optical prisms located on either side of a plane perpendicular to said planar front face, said supporting means for the optical element comprising a carrier, an opening in said carrier for receiving said element, a peripheral flange internal with said element body intermediate its length and spaced from said front face, said flange projecting outwardly at an angle to the body, said optical element having a sliding fit for retaining the optical element in said carrier opening to be replaceably insertable therein, said flange forming means for abutting with the carrier whereby the optical element is axially locatable in said carrier opening by said abutment means to leave said cylindrical body partially projecting therefrom and said front face spaced from the carrier, said abutting means including means for locating the element rotationally in said carrier.

6. An applanating member for an applanation tonometer according to claim 5, wherein said flange includes a front face and a rear face extending away from said cylindrical body, said rear face forming with said body an annular pocket for receiving the tubular carrier.

7. An optical element for an applanation tonometer comprising a light-transmitting body, a flat front face at one end of said body, a pair of optical prisms formed on a second end of said body opposite said one end, said prisms being located on opposite sides of a plane perpendicular to said planar front face, a flange on said body intermediate the length of the body for abutting location with a tubular carrier in which the element is intended to be mounted, said flange having a front face and a rear face extending away from said body, said rear face forming with said body an annular pocket for receiving said tubular carrier.

8. An optical element according to claim 7 wherein the body and the flange have respective transverse dimensions, the transverse dimensions of said flange being at least 50% greater than the transverse dimensions of the body.

9. An optical element for an applanation tonometer comprising a light-transmitting body, a flat front face at one end of said body, a pair of optical prisms formed on a second end of said body opposite said one end, said prisms being located on opposite sides of a plane perpendicular to said flat front face of said body, a flange having a front face and a rear face, said front face of said flange being displaced from said flat face of said body such that a portion of an exterior surface of said body extends between the front face of the body and the front face of the flange, said front face of the flange extending away from said body protuberant from said exterior surface of said body, wherein said rear face of said flange is oblique to said exterior surface of said body.

10. An optical element for an applanation tonometer according to claim 9 wherein the body and the flange have respective radial dimensions of which the radial dimension of the flange is at least 50% greater than a radial dimension of the body.

11. An optical element for an applanation tonometer according to claim 9 wherein said portion of the exterior surface of said body is cylindrical.

12. An optical element for an applanation tonometer according to claim 9 wherein said front face of said flange is oblique to said exterior surface of said body.

* * * * *